United States Patent
Lee et al.

(10) Patent No.: US 11,058,695 B2
(45) Date of Patent: Jul. 13, 2021

(54) INHIBITOR OF CARBAPENEM-HYDROLYZING CLASS D BETA-LACTAMASES

(71) Applicant: MYONGJI UNIVERSITY INDUSTRY AND ACADEMIA COOPERATION FOUNDATION, Gyeonggido (KR)

(72) Inventors: Sang Hee Lee, Gyeonggi-do (KR); Jung Hun Lee, Gyeonggido (KR); Jeong Ho Jeon, Incheon (KR)

(73) Assignee: MYONGJI UNIVERSITY INDUSTRY AND ACADEMIA COOPERATION FOUNDATION, Gyeonggido (KR)

( * ) Notice: Subject to any disclaimer, the term of this patent is extended or adjusted under 35 U.S.C. 154(b) by 67 days.

(21) Appl. No.: 16/677,976

(22) Filed: Nov. 8, 2019

(65) Prior Publication Data

US 2021/0137954 A1    May 13, 2021

(51) Int. Cl.
*A61K 31/69* (2006.01)
*A61P 31/04* (2006.01)
*A61K 45/06* (2006.01)

(52) U.S. Cl.
CPC .............. *A61K 31/69* (2013.01); *A61K 45/06* (2013.01)

(58) Field of Classification Search
CPC .................................. A61K 31/69; A61P 31/04
USPC ........................................................ 514/64
See application file for complete search history.

(56) References Cited

U.S. PATENT DOCUMENTS

| | | | |
|---|---|---|---|
| 6,448,238 B1* | 9/2002 | Shoichet | A61K 31/18 514/330 |
| 2009/0227541 A1* | 9/2009 | Baker | A61P 31/02 514/64 |
| 2014/0171390 A1* | 6/2014 | Burns | A61P 43/00 514/64 |
| 2015/0119363 A1* | 4/2015 | Dudley | A61K 31/551 514/64 |

* cited by examiner

*Primary Examiner* — Raymond J Henley, III
(74) *Attorney, Agent, or Firm* — The PL Law Group, PLLC

(57) ABSTRACT

A compound having Formula I is an inhibitor of carbapenem-hydrolyzing class D beta-lactamases. The compound inhibits the activities of clinically-important and emerging subgroups of carbapenem-hydrolyzing class D beta-lactamases. A method of treating a bacterial infection includes administering to a subject suffering from a bacterial infection a composition including an effective amount of the compound having Formula I or the pharmaceutically acceptable salt thereof.

17 Claims, 2 Drawing Sheets
Specification includes a Sequence Listing.

FIG. 1

¹H-NMR spectra (PLPBA)

FIG. 2

¹³C-NMR spectra (PLPBA)

SEQUENCE LISTING

<160> NUMBER OF SEQ ID NOS: 24

<210> SEQ ID NO 1
<211> LENGTH: 66
<212> TYPE: DNA
<213> ORGANISM: Artificial Sequence
<220> FEATURE:
<223> OTHER INFORMATION: Primer

<400> SEQUENCE: 1
atacatatgc accatcatca tcatcatgac gacgacgaca agcagattgt tcaaggacat    60
aatcag    66

<210> SEQ ID NO 2
<211> LENGTH: 40
<212> TYPE: DNA
<213> ORGANISM: Artificial Sequence
<220> FEATURE:
<223> OTHER INFORMATION: Primer

<400> SEQUENCE: 2
gagctcgagt taaataatat tcagctgttt taatgatttc    40

<210> SEQ ID NO 3
<211> LENGTH: 74
<212> TYPE: DNA
<213> ORGANISM: Artificial Sequence
<220> FEATURE:
<223> OTHER INFORMATION: Primer

<400> SEQUENCE: 3
atacatatgc accatcatca tcatcatgac gacgacgaca agcatatttc ttctcagcaa    60
catgaaaaag ctat    74

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
gagctcgagt taaatgattc caagattttc tagcgactta t    41

```
<210> SEQ ID NO 5
<211> LENGTH: 71
<212> TYPE: DNA
<213> ORGANISM: Artificial Sequence
<220> FEATURE:
<223> OTHER INFORMATION: Primer

<400> SEQUENCE: 5
atacatatgc accatcatca tcatcatgac gacgacgaca aggaatggca agaaaacaaa      60
agttggaatg c                                                          71

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
gagctcgagc tagggaataa tttttccctg tttgagcact tc                        42

<210> SEQ ID NO 7
<211> LENGTH: 67
<212> TYPE: DNA
<213> ORGANISM: Artificial Sequence
<220> FEATURE:
<223> OTHER INFORMATION: Primer

<400> SEQUENCE: 7
atacatatgc accatcatca tcatcatgac gacgacgaca agaatccaaa tcacagcgct      60
tcaaaat                                                               67

<210> SEQ ID NO 8
<211> LENGTH: 44
<212> TYPE: DNA
<213> ORGANISM: Artificial Sequence
<220> FEATURE:
<223> OTHER INFORMATION: Primer

<400> SEQUENCE: 8
gagctcgagc tataaaatac ctaattgttc taaactttta taag                      44

<210> SEQ ID NO 9
<211> LENGTH: 64
<212> TYPE: DNA
<213> ORGANISM: Artificial Sequence
<220> FEATURE:
<223> OTHER INFORMATION: Primer

<400> SEQUENCE: 9
gatatacata tgcaccatca tcatcatcat gacgacgacg acaagcatag tatgagtcga      60
gcaa                                                                  64

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
caggagctcg agttataaat aatgaaaaac acc                                  33
```

```
<210> SEQ ID NO 11
<211> LENGTH: 67
<212> TYPE: DNA
<213> ORGANISM: Artificial Sequence
<220> FEATURE:
<223> OTHER INFORMATION: Primer

<400> SEQUENCE: 11
atacatatgc accatcatca tcatcatgac gacgacgaca agaatccaaa tcacagcgct    60
tcaaaat                                                             67

<210> SEQ ID NO 12
<211> LENGTH: 43
<212> TYPE: DNA
<213> ORGANISM: Artificial Sequence
<220> FEATURE:
<223> OTHER INFORMATION: Primer

<400> SEQUENCE: 12
gagctcgagc tataaaatac ctaattgttc taagctttta taa                     43

<210> SEQ ID NO 13
<211> LENGTH: 67
<212> TYPE: DNA
<213> ORGANISM: Artificial Sequence
<220> FEATURE:
<223> OTHER INFORMATION: Primer

<400> SEQUENCE: 13
atacatatgc accatcatca tcatcatgac gacgacgaca agaatcagca acatgaaaaa    60
gccatta                                                             67

<210> SEQ ID NO 14
<211> LENGTH: 44
<212> TYPE: DNA
<213> ORGANISM: Artificial Sequence
<220> FEATURE:
<223> OTHER INFORMATION: Primer

<400> SEQUENCE: 14
gagctcgagt tatataatcc ctaaattctc taatgattta taag                    44

<210> SEQ ID NO 15
<211> LENGTH: 64
<212> TYPE: DNA
<213> ORGANISM: Artificial Sequence
<220> FEATURE:
<223> OTHER INFORMATION: Primer

<400> SEQUENCE: 15
gatatacata tgcaccatca tcatcatcat gacgacgacg acaaggcgca agaaggcacg    60
ctag                                                                64

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
caggagctcg agttatcgcg cagcgtccga g                                  31

<210> SEQ ID NO 17
```

<211> LENGTH: 70
<212> TYPE: DNA
<213> ORGANISM: Artificial Sequence
<220> FEATURE:
<223> OTHER INFORMATION: Primer

<400> SEQUENCE: 17
ataccatggg ccaccatcat catcatcatg acgacgacga caagaaaaat caccagcaac    60
aaagtgctca                                                          70

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
gagctcgagt taaattatcc ccagtgctgt cagactt                             37

<210> SEQ ID NO 19
<211> LENGTH: 68
<212> TYPE: DNA
<213> ORGANISM: Artificial Sequence
<220> FEATURE:
<223> OTHER INFORMATION: Primer

<400> SEQUENCE: 19
atacatatgc accatcatca tcatcatgac gacgacgaca agcgagaaac tgagattcct    60
ttattatt                                                            68

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
gagctcgagt tatcttaaat aaaaaaatag acccaatttg t                        41

<210> SEQ ID NO 21
<211> LENGTH: 70
<212> TYPE: DNA
<213> ORGANISM: Artificial Sequence
<220> FEATURE:
<223> OTHER INFORMATION: Primer

<400> SEQUENCE: 21
catataccat gggccaccat catcatcatc atgacgacga cgacaagggt tcaattacag    60
aaaatacgtc                                                          70

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
caggagctcg agttagccac caatgatgcc caca                                34

<210> SEQ ID NO 23
<211> LENGTH: 69

```
-continued

<212> TYPE: DNA
<213> ORGANISM: Artificial Sequence
<220> FEATURE:
<223> OTHER INFORMATION: Primer

<400> SEQUENCE: 23
atacatatgc accatcatca tcatcatgac gacgacgaca agggttgtgt ttatgattca      60
aaactacaa                                                              69

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
gtgctcgagt tatcttaaat aaaaaaatag acccaatttg                            40
```

INHIBITOR OF CARBAPENEM-HYDROLYZING CLASS D BETA-LACTAMASES

1. FIELD OF THE INVENTION

The invention relates to the inhibition of carbapenem-hydrolyzing class D beta-lactamases (CHDL). The compound is therefore useful in potentiating the effects of beta-lactam antibiotic agents (beta-lactams) and can be used in combination with beta-lactams in the prevention and treatment of bacterial infections.

2. BACKGROUND

Beta-lactamases are bacterial enzymes that hydrolytically inactivate beta-lactams and are a major cause of the emergence of pathogenic bacteria resistant to beta-lactams such as penicillins, cephalosporins, monobactams, and carbapenems that are a class of highly effective antibiotic agents commonly used for the treatment of severe or high-risk bacterial infections.

Based on the sequence homology, beta-lactamases are grouped into four molecular classes A, B, C, and D (Bush, et al., *Antimicrob. Agents Chemother.*, 54, 969-976 (2010); Galleni, et al., *Antimicrob. Agents Chemother.*, 45, 660-663 (2001)).

Classes A, C, and D of beta-lactamases are serine-based enzymes in which a covalent acyl-enzyme intermediate is formed.

Carbapenemases are the most versatile family of beta-lactamases and are able to hydrolyze carbapenems and other beta-lactams (Queenan, et al., *Clin. Microbiol. Rev*, 20, 440-458 (2007)). According to their dependency on divalent cations for enzyme activation, carbapenemases can be divided into non-metallo-carbapenemases (zinc-independent classes A, C, and D) and metallo-carbapenemases (zinc-dependent class B) (Lee, et al., *Res. J. Microbiol.*, 1, 1-22 (2006)). Carbapenems (imipenem, meropenem, biapenem, ertapenem, and doripenem) have a penicillin-like five-membered ring, but the sulfur at C-1 in the five-membered ring is replaced with a carbon atom and a double bond between C-2 and C-3 is introduced (Moellering, et al., *J. Antimicrob. Chemother*, 24, 1-7 (1989)). Carbapenems have the broadest spectra of antimicrobial activity among all beta-lactams and are primarily used to treat infections by aerobic Gram-negative bacteria. The emergence and spread of acquired carbapenem resistance due to carbapenemases are a major concern of the public health and is considered a global sentinel event (Richet, et al., *Emerg. Infect. Dis.*, 7: 319-322 (2001)).

Class D beta-lactamases, known as OXA-type enzymes (OXA stands for oxacillinase), are represented by more than 850 genetically. Class D carbapenemases were also known as carbapenem-hydrolyzing class D beta-lactamases (CHDLs). Based on their amino acid sequence identity, CHDLs have been subdivided into several subgroups (OXA-23, OXA-24/40, OXA-48, OXA-51, OXA-55, OXA-58, OXA-60, OXA-62, OXA-134, OXA-143, OXA-211, OXA-213, OXA-214, OXA-229, OXA-235, and OXA-372 subgroups) (Antonelli, et al., *J. Antimicrob. Chemother.*, 70, 2749-2756 (2015); Evans, et al., *Clin. Microbiol. Rev.*, 27, 241-263 (2014)). They have been mainly identified in *Acinetobacter baumannii* and *Pseudomonas aeruginosa* (Evans, et al., *Clin. Microbiol. Rev*, 27, 241-263 (2014)). Six CHDLs belonging to the OXA-23, OXA-24/40, OXA-48, OXA-51, OXA-58, and OXA-143 subgroups are of major clinical importance due to their wide dissemination in bacterial pathogens (Antunes, et al., *Antimicrob. Agents Chemother.*, 58, 2119-2125 (2014)). CHDLs are most problematic clinically, as they produce resistance to the antibiotics of last resort, carbapenems, severely limiting therapeutic options.

Phenylboronic acid (PBA) was reported by Rettig, et al., *Can. J. Chem.*, 55, 3071-3075 (1977). Twelve substituted phenylboronic acids, including 2-formylphenylboronate (2FORMB), 4-formyl phenylboronate (4 FORMB), and 4-methylphenylboronate (4MEPB), were reported by Beesley, et al., *Biochem. J.*, 209, 229-233 (1983). Boric acid, PBA, m-aminophenyboronate (MAPB), and tetraphenylboronic acid was reported by Amicosante, et al., *J. Chemotherapy*, 1, 394-398 (1989). In particular, m-(dansylamidophenyl)-boronic acid (NSULFB) has been reported to be a submicromolar inhibitor of the *Enterobacter cloacae* P99 beta-lactamase (Dryjanski, et al., *Biochemistry*, 34, 3561-3568 (1995)). To design a novel alkylboronic acid inhibitor (1R)-1-acetamido-2-(3-carboxyphenyl)ethane boronic acid with high affinity for TEM-1 enzyme, the crystallographic structure of a mutant TEM-1 enzyme-penicillin G complex was used (Strynadka, et al., *Nat. Struct. Biol.*, 3: 688 (1996)). These phenylboronic acid derivatives have good potency in reversibly inhibiting class A and C beta-lactamases. Avibactam (formerly NXL104) and a diazabicyclooctane (DBO, non-lactam class) derivative antibiotic, also have good potency in reversibly inhibiting serine beta-lactamase enzymes including class A (mainly extended-spectrum beta-lactamases (ESBLs) and *Klebsiella pneumonia* carbapenemases (KPCs)), class C, and partial class D (OXA-1, OXA-10, and OXA-48 subgroup) beta-lactamases.

However, all reported compounds have not been proven to inhibit five major clinically-important CHDLs subgroups (OXA-23, OXA-24/40, OXA-51, OXA-58, and OXA-143 subgroups) and emerging CHDL subgroups.

Therefore, there is an imperative need to develop novel CHDL inhibitors with broad-spectrum functionality to inhibit all six major clinically-important CHDLs subgroups and emerging CHDL subgroups.

SUMMARY

The invention relates to an inhibitor compound (formula (I)). In particular, the invention provides CHDL inhibitor, a non-beta-lactam inhibitor of CHDLs, having the formula (I):

Formula I

The compound described above has been found to inhibit six clinically-important subgroups of CHDLs and emerging CHDL subgroups. Therefore, this compound is useful in the method of inhibiting CHDLs.

According to an aspect of the present invention, a method of treating a bacterial infection may include preparing a composition having Formula I or a pharmaceutically acceptable salt thereof, and administering to a subject suffering from the bacterial infection, the composition comprising an effective amount of the compound having Formula I or the pharmaceutically acceptable salt thereof.

According to an aspect of the present invention, the composition may further include a beta-lactam antibiotic agent.

According to an aspect of the present invention, the antibiotic agent may be selected from the group consisting of penicillins, cephems, carbapenems, penems, and monobactams.

According to an aspect of the present invention, the antibiotic agent may be selected from the group consisting of penicillins, cephalosporins, cephamycins, monobactams, carbapenems, and a combination thereof.

According to an aspect of the present invention, the method may further include administering a beta-lactam antibiotic agent to the subject, prior to, simultaneously, or subsequent to administering the composition to the subject.

According to an aspect of the present invention, the composition may further include a pharmaceutically acceptable carrier.

According to an aspect of the present invention, the infection is caused by pathogenic bacteria resistant to beta-lactam.

According to an aspect of the present invention, the compound having Formula I may be prepared by a process including preparing a solution comprising 3-bromophenol, phenethyl alcohol, and triphenylphosphine, adding diisopropyl azodicarboxylate to the solution to prepare 1-bromo-3-(2-phenylethoxy)benzene, and adding n-butyllithium to the 1-bromo-3-(2-phenylethoxy)benzene, and, then, adding triisopropyl borate to obtain the compound having Formula I.

According to an aspect of the present invention, a method of inhibiting carbapenem-hydrolyzing class D beta-lactamases (CHDLs), the method includes preparing a composition having Formula I or a pharmaceutically acceptable salt thereof, and administering to a subject in need thereof the composition including an effective amount of the compound having Formula I or the pharmaceutically acceptable salt thereof, wherein the carbapenem-hydrolyzing class D beta-lactamases comprises OXA-23, OXA-24/40, OXA-51, OXA-58, and OXA-143.

According to an aspect of the present invention, the carbapenem-hydrolyzing class D beta-lactamases may further include at least one of the subgroups of OXA-48, OXA-97, OXA-109, OXA-210, OXA-211, OXA-229, OXA-240, and OXA-418.

DETAILED DESCRIPTION

Hereinafter embodiments of the present invention will be described in detail with reference to accompanying drawings.

According to one or more embodiments of the present invention, a composition including the compound of Formula I may be used an inhibitor of CHDLs. Unlike all the reported compounds which have not been proven to inhibit five major clinically-important CHDLs subgroups (OXA-23, OXA-24/40, OXA-51, OXA-58, and OXA-143 subgroups), the compound of Formula I shows broad-spectrum functionality to inhibit all six major clinically-important CHDLs subgroups and emerging CHDL subgroups.

Therefore, compared with the conventional CHDL inhibitors, the compound of Formula I is more effective in inhibiting CHDLs so that the compound of Formula I may be more useful for the treatment of bacterial infections.

Since the beta-lactamases of pathogenic bacteria resistant to beta-lactam antibiotics are inactivated by administering the compound of Formula I, the treatment with the antibiotics may be more effectively performed.

Beta-lactam antibiotics (β-lactam antibiotics) are the antibiotic agents that contain a beta-lactam ring in their molecular structure. The beta-lactam antibiotics include, but not limited to, penicillins, cephems, carbapenems, penems, and monobactams. According to an embodiment of the present application, the beta-lactam antibiotics are penicillins, cephalosporins, cephamycins, monobactams, and/or carbapenems.

The composition including the compound of Formula I may be administered either orally or parenterally, and, in case of parenteral administration, the administration can be made by topical application on skin, intravenous injection, subcutaneous injection, muscular injection, intraperitoneal injection, or transdermal administration.

The composition is administered in a pharmaceutically effective amount. As described herein, the expression "pharmaceutically effective amount" means an amount sufficient for treating a bacterial infection that can be applied for a medical treatment. The effective dose level may be determined based on a type or severeness of an infection, activity of a pharmaceutical, sensitivity to a pharmaceutical, administration period, administration route, excretion ratio, time period for therapy, elements including a pharmaceutical used in combination, and other elements that are well known in the medical field. The composition may be administered to a subject, before, simultaneously with, or after administering the beta-lactam antibiotics. The composition can be administered as a separate therapeutic agent, or it can be used in combination with other therapeutic agent. It can be administered in order or simultaneously with a conventional therapeutic agent. It can be also administered as single-dose or multi-dose. It is important to administer an amount which allows obtainment of the maximum effect with minimum dose while considering the all of the aforementioned elements without having any side effect, and the dosage can be easily determined by a person skilled in the pertinent art.

The composition according to an embodiment of the present invention may further include a pharmaceutically acceptable carrier. Included in the carrier are lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propylhydroxy benzoate, talc, magnesium stearate, and mineral oil that are commonly used for having a preparation, but it is not limited thereto. The composition according to an embodiment of the present invention may additionally include a lubricant, a wetting agent, a sweetener, a flavoring agent, an emulsifier, a suspending agent, and a preservative.

The composition of an embodiment of the present invention may be prepared in various formulations including an oral formulation and a parenteral formulation. In case of producing a preparation, production is made by using a diluent or a vehicle such as filler, bulking agent, binding agent, moisturizing agent, disintegrating agent, or surfactant that are commonly used for producing a preparation. As for the solid preparation for oral administration, a tablet, a pill, a powder preparation, a granule, a capsule or the like are included, and such solid preparation is produced by mixing at least one compound with one or more vehicles such as starch, calcium carbonate, sucrose, lactose, or gelatin. Furthermore, other than simple vehicles, a lubricating agent such as magnesium stearate or talc is also used. As for the liquid preparation for oral administration, a suspension, a solution preparation for internal use, an emulsion, a syrup preparation, or the like can be mentioned. Other than water or liquid paraffin as a commonly used simple diluent, various kinds of a vehicle such as moisturizing agent, sweetening agent, aromatic agent, or preservatives may be included. Examples of a preparation for parenteral administration include a sterilized aqueous solution, a non-soluble agent, a suspension agent, an emulsion, a freeze-drying agent, and a suppository agent. As a water insoluble solvent or a suspending agent, propylene glycol, polyethylene glycol, or vegetable oil such as olive oil, and injectable ester such as ethylolate can be used. As a base for a suppository, witepsol, macrogol, tween 61, cacao fat, laurin fat, glycerogelatin, or the like can be used.

Hereinbelow, the present invention is explained in greater detail in view of the Examples. However, the following Examples are given only for specific explanation of the present invention and it wound be evident to a person who has common knowledge in the pertinent art that the scope of the present invention is not limited by them.

Structure-based virtual screening using ICM-VLS software was used to find compounds inhibiting CHDLs (see Example 1 below). CHDLs for use in such screening were purified from bacterial sources. The ability ($IC_{50}$ value) of the screened compounds to inhibit CHDL activities was determined using the standard enzyme inhibition assay (see Example 4 below; Page, *Biochem. J.*, 295, 295-304 (1993)). A new CHDL inhibitor (formula (I)) was found.

Example 1

Virtual Library Screening

To find compounds inhibiting the OXA-48 (the most clinically-important CHDL), structure-based virtual screening was performed using ICM-VLS software. The crystallographic structure of OXA-48 (PDB ID, 4S2P) was analyzed using the PocketFinder algorithm available in the Internal Coordinate Mechanics (ICM) software program (Molsoft, LLC).

The protein structure was prepared by three-dimensional (3D) protonation, deletion of water molecules, and energy minimization using the ICM force field and distance-dependent dielectric potential with an RMS (root mean square) gradient of 0.1 Å.

A ligand-binding site was defined as a subset region of 13.0 Å around the active site cleft and was selected as the target site for virtual library screening (VLS) using ICM-VLS software (Molsoft, LLC). ICM-VLS uses global optimization with a biased probability Monte Carlo conformational search to rapidly dock fully flexible, full-atom models of the ligands to a set of grid potential maps calculated from the coordinates of the atoms in the protein receptor. Each ligand-docking conformation is then evaluated with a scoring function. The ICM-scoring function integrates van der Waals energy, electrostatics, hydrogen bonding, conformational entropy loss, and solvation electrostatic energy change (Abagyan, et al., *J. Mol. Biol.*, 235, 983-1002 (1994)). ICM-VLS was used to dock the entire set of 1,720,909 compounds from the Enamine Library using default ICM-docking parameters on three 3.0-GHz Intel Xeon processors. After three separate docking runs, the resulting compounds with a docking score of <−55 were further filtered by selecting those with extensive hydrogen bonds and van der Waals contacts, followed by hierarchical clustering for a diversity of scaffolds, resulting in the identification of 55 compounds highly structurally and chemically compatible with the target OXA-48 ligand-binding site. Seven compounds with the highest molecular docking scores were selected and were purchased from the Enamine (http://www.enamine.net/).

$IC_{50}$ values of seven compounds were determined as described below. The screened 7 compounds were dissolved in 100% DMSO at 10 mM. More diluted stocks were prepared as necessary. OXA-48 activity was determined by monitoring the change of absorbance at 482 nm using the characteristic molecular extinction coefficient ($\Delta\varepsilon_{482}$=15,900 $M^{-1}$ $cm^{-1}$) of nitrocefin (Oxoid, Hampshire, UK) by a Shimazu UV-1650PC spectrophotometer. Up to 5% DMSO, no influence on the enzyme activity of OXA-48 was observed. The assays were conducted in 10 mM MES (pH 6.8) containing OXA-48 (103 pM), 50 mM $NaHCO_3$, and 20 µg/mL bovine serum albumin. After 5 min of pre-incubation of the purified OXA-48 and each inhibitor at 30° C., the enzymatic reaction was started by adding nitrocefin (100 µM). Residual velocities were determined after 5 minutes. The first 120 s of each reaction was used to measure initial rates. Data were evaluated using Microsoft Excel. Concentration-dependent inhibition of OXA-48 was measured using different concentrations of seven compounds resulting from two-fold dilution series. Reaction progress at every concentration of seven compounds was measured in triplicates. $IC_{50}$ values were calculated using 4-parameter log fits using XL Fit curve fitting software (www.idbs.com) for Excel using the following equation:

$$y = A + \frac{B - A}{1 + \left(\frac{x}{IC_{50}}\right)^{slope}}$$

where y is the remaining enzyme activity (in %) and x is the corresponding concentration. The fitted $IC_{50}$ parameter is defined as the concentration giving a response half way between the fitted top (B) and bottom (A) of the curve. Out of the seven compounds, only compound 1 showed $IC_{50}$ value (154.8 µM) (Table 1).

TABLE 1

$IC_{50}$ values on OXA-48 of the screened compounds.

| Compound | $IC_{50}$ (µM) |
|---|---|
| 1 | 154.8 |
| 2 | NI[a] |
| 3 | NI |
| 4 | NI |
| 5 | NI |
| 6 | NI |
| 7 | NI |

[a]NI, no inhibition.

Example 2

Synthesis and Characterization of Compound 1

Organometallic reactions were performed under argon atmosphere in oven-dried glassware and using anhydrous solvents. Anhydrous tetrahydrofuran (THF) and diethyl ether were obtained by standard methods and freshly distilled under argon from sodium benzophenone ketyl before use. All starting chemicals and reagents were commercially available. Chromatographic purification of the compounds was performed on silica gel (particle size 0.05-0.20 mm). OptiMelt automatic melting point system (MMPA100, Stanford Research Systems, Sunnyvale, Calif.) was used for defining a melting point. $^1$H-NMR and $^{13}$C-NMR spectra were recorded on a Bruker Avance 500 (500 MHz for $^1$H and 125 MHz for $^{13}$C) spectrometer in deuterated dimethyl sulfoxide (DMSO-d$_6$) solutions. Chemical shifts (δ) are reported in ppm downfield from tetramethylsilane (TMS) as internal standard (s: singlet, d: doublet, t: triplet, m: multiplet, br s: broad signal). The purity of the obtained compounds was checked by LC/MS on an Agilent 1100 instrument. The purity of all tested compounds was above 95%.

Synthesis of [3-(2-Phenylethoxy)phenyl]boronic Acid: PLPBA (Compound 1)

An exemplary synthesis of the compound of Formula I is as follows:

Scheme 1: Synthesis of PLPBA.

(a) i. PhA; ii. Ph$_2$P, DIAD
(b) i. BuLi; ii. B(Opr-i)$_3$; iii. HCl

Step 1:

3-Bromophenol (0.013 mol), phenethyl alcohol (0.013 mol), and triphenylphosphine (0.016 mol) were dissolved in 50 mL of anhydrous THF. Diisopropyl azodicarboxylate (DIAD, 0.016 mol) was added dropwise to this solution at 0° C. with constant stirring. After the addition was complete the mixture was allowed to warm to RT and was stirred overnight. The solvent was evaporated and the residue was taken into the ether (100 mL), washed continuously with NaOH solution and water, and dried (MgSO$_4$). The ether was removed in vacuo and the residue was purified by flash chromatography (silica gel, hexane/ethyl acetate 4:1).

Figure 1:
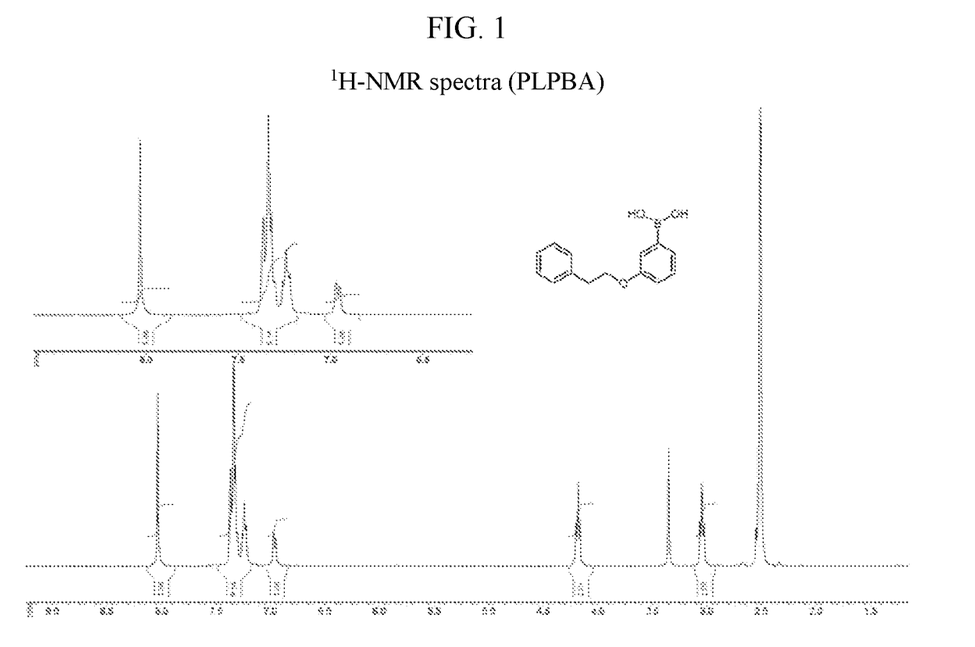
FIG. 1 shows $^1$H-NMR spectra of [3-(2-Phenylethoxy)phenyl]boronic acid.
Figure 2:
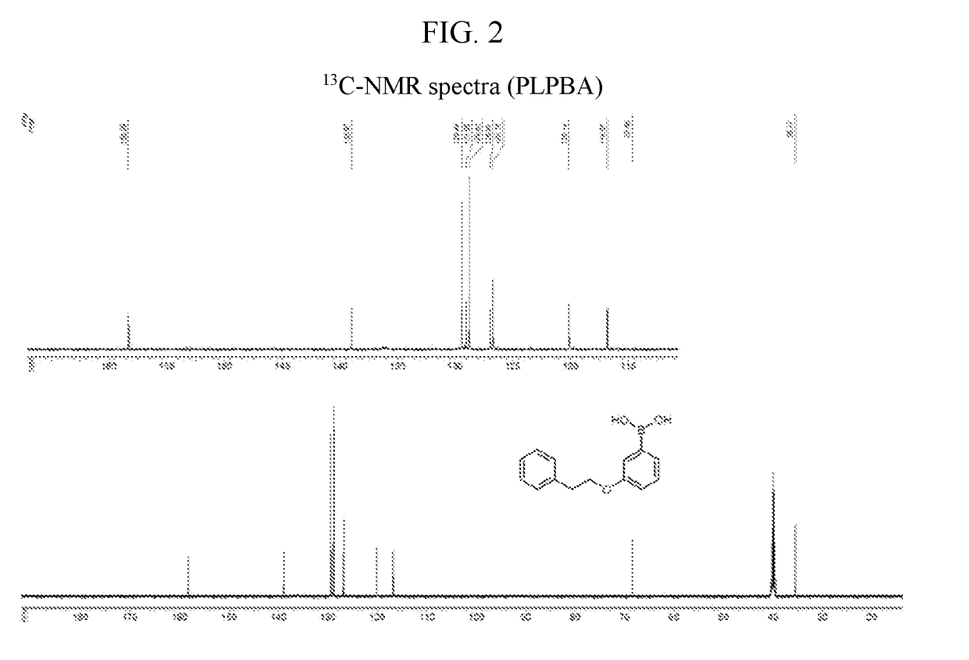
FIG. 2 shows $^{13}$C-NMR spectra of [3-(2-Phenylethoxy)phenyl]boronic acid.

Step 2:

to A stirred solution of the bromide [1-bromo-3-(2-phenylethoxy)benzene, 0.009 mole] in 100 mL of THF-toluene mixture (1:1 v/v) was cooled to −80° C. and 0.010 mol of n-butyllithium in hexane (2.5 M) was added dropwise, while maintaining the reaction mixture temperature below −70° C. Upon completion of the addition, the reaction mixture was stirred at −80° C. for 15 min and then 0.011 mol of triisopropyl borate was added at once. The reaction mixture was allowed to warm slowly to ambient temperature and was stirred overnight. Ice-water (150 mL) and concentrated hydrochloric acid (10 mL) were added to the mixture and the organic layer was separated. It was evaporated in vacuo, the residue was dissolved in 100 mL of 5% aqueous NaOH and washed with toluene (2×30 mL). The aqueous phase was acidified to pH 2 with concentrated hydrochloric acid and the precipitate formed was filtered and dried to give the target compound as a white powder. Mp=130-133° C. LC/MS: MH+243. $^1$H-NMR (500 MHz, DMSO): 3.09 (t, 2H, CH2), 4.16 (t, 2H, CH2), 6.97 (d, 1H, 4-H), 7.20-7.40 (m, 8H, Ph+2,5,6-H), 8.08 (s, 2H, OH). (FIG. 1) $^{13}$C-NMR (125 MHz, DMSO): 35.6 (CH2), 68.5 (CH2), 116.8 (4-C), 120.1 (5-C), 125.7 (Ph), 126.0 (2-C), 128.8 (Ph), 129.1 (1-C), 129.4 (Ph), 139.0 (Ph), 158.3 (3-C) (FIG. 2).

Example 3

Protein Production and Purification

Nine DNA templates encoding bla$_{OXA-23}$ gene (GenBank ID:AJ132105), bla$_{OXA-24/40}$ gene (GenBank ID:AJ239129), bla$_{OXA-48}$ gene (GenBank ID:AY236073), bla$_{OXA-51}$ gene (GenBank ID:AJ309734), bla$_{OXA-97}$ gene (GenBank ID:EF102240), bla$_{OXA-199}$ gene (GenBank ID:EF650035), bla$_{OXA-143}$ gene (GenBank ID:GQ861437), bla$_{OXA-211}$ gene (GenBank ID:JN861779), and bla$_{OXA-229}$ gene (GenBank ID:JQ422052), which are codon optimized for *E. coli*, were synthesized and purchased from IDT (Integrated DNA Technologies, Coralville, Iowa, USA). The DNA templates were amplified by PCR using suitable primer pairs (Table 2). The bla$_{OXA-210}$ gene (GenBank ID:JF795487) from *Pseudomonas aeruginosa* PAE0831, the bla$_{OXA-240}$ gene (GenBank ID:JX089628) from *P. aeruginosa* WK28, and the bla$_{OXA-418}$ gene (GenBank ID:KJ997966) from *Acinetobacter baumannii* ABA031 were cloned after PCR amplification with primer pairs (Table 2) and then sequenced. The amplified DNA and pET-28a(+) or pET-30a(+) vector (Novagen, Madison, Wis., USA) were double-digested with NdeI (or NcoI) and XhoI, with digested DNA then ligated into the digested vector. After verifying the DNA sequences, the plasmids, pET-30a(+)/His$_6$-bla$_{OXA-23}$, pET-30a(+)/His$_6$-bla$_{OXA-24/40}$, pET-30a(+)/His$_6$-bla$_{OXA-51}$, pET-30a(+)/His$_6$-bla$_{OXA-97}$, pET-30a(+)/His$_6$-bla$_{OXA-109}$, pET-30a(+)/His$_6$-bla$_{OXA-143}$, pET-30a(+)/His$_6$-bla$_{OXA-210}$, pET-28a(+)/His$_6$-bla$_{OXA-211}$, pET-30a(+)/His$_6$-bla$_{OXA-229}$, pET-28a(+)/His$_6$-bla$_{OXA-240}$, and pET-30a(+)/His$_6$-bla$_{OXA-418}$ were individually transformed into *E. coli* BL21 (DE3) cells. Each of the histidine-tagged proteins, OXA-23, OXA-24/40, OXA-48, OXA-51, OXA-97, OXA-109, OXA-143, OXA-210, OXA-211, OXA-229, OXA-240, and OXA-418 were prepared as previously described (Park, et al., *J. Glob. Antimicrob. Resist.*, 14, 302-305 (2018)).

TABLE 2

Nucleotide sequences of the oligonucleotides used for PCR amplification to express twelve genes encoding CHDLs.

| Name | Primer name[a] | Sequences (5'-3')[b] |
|---|---|---|
| OXA-23 | NdeI-HIS-EK-OXA-23-F | ATA*CATATG*CACCATCATCATCATCATGACGAC GACGACAAGCAGATTGTTCAAGGACATAATC AG (SEQ ID NO: 1) |
|  | XhoI-OXA-23-R | GAG*CTCGAG*TTAAATAATATTCAGCTGTTTTAA TGATTTC (SEQ ID NO: 2) |
| OXA-24/40 | NdeI-HIS-EK-OXA-24/40-F | ATA*CATATG*CACCATCATCATCATCATGACGAC GACGACAAGCATATTTCTTCTCAGCAACATGA AAAAGCTAT (SEQ ID NO: 3) |
|  | XhoI-OXA-40-R | GAG*CTCGAG*TTAAATGATTCCAAGATTTTCTAG CGACTTAT (SEQ ID NO: 4) |
| OXA-48 | NdeI-HIS-EK-OXA-48-F | ATA*CATATG*CACCATCATCATCATCATGACGAC GACGACAAGGAATGGCAAGAAAACAAAAGTT GGAATGC (SEQ ID NO: 5) |
|  | XhoI-OXA-48-R | GAG*CTCGAG*CTAGGGAATAATTTTTTCCTGTTT GAGCACTTC (SEQ ID NO: 6) |
| OXA-51 | NdeI-HIS-EK-OXA-51-F | ATA*CATATG*CACCATCATCATCATCATGACGAC GACGACAAGAATCCAAATCACAGCGCTTCAA AAT (SEQ ID NO: 7) |
|  | XhoI-OXA-51-R | GAG*CTCGAG*CTATAAAATACCTAATTGTTCTAA ACTTTTATAAG (SEQ ID NO: 8) |
| OXA-97 | NdeI-His-EK-OXA97-F | GATATA*CATATG*CACCATCATCATCATCATGAC GACGACGACAAGCATAGTATGAGTCGAGCAA (SEQ ID NO: 9) |
|  | XhoI-OXA97-R | CAGGAG*CTCGAG*TTATAAATAATGAAAAACAC C (SEQ ID NO: 10) |
| OXA-109 | NdeI-His-EK-OXA109-F | ATA*CATATG*CACCATCATCATCATCATGACGAC GACGACAAGAATCCAAATCACAGCGCTTCAA AAT (SEQ ID NO: 11) |
|  | XhoI-OXA109-R | GAG*CTCGAG*CTATAAAATACCTAATTGTTCTAA GCTTTTATAA (SEQ ID NO: 12) |
| OXA-143 | NdeI-HIS-EK-OXA-143-F | ATA*CATATG*CACCATCATCATCATCATGACGAC GACGACAAGAATCAGCAACATGAAAAAGCCA TTA (SEQ ID NO: 13) |
|  | XhoI-OXA-143-R | GAG*CTCGAG*TTATATAATCCCTAAATTCTCTAA TGATTTATAAG (SEQ ID NO: 14) |
| OXA-210 | NdeI-HIS-EK-OXA-210-F | GATATA*CATATG*CACCATCATCATCATCATGAC GACGACGACAAGGCGCAAGAAGGCACGCTAG (SEQ ID NO: 15) |
|  | XhoI-OXA-210-R | CAGGAG*CTCGAG*TTATCGCGCAGCGTCCGAG (SEQ ID NO: 16) |
| OXA-211 | NcoI-HIS-EK-OXA-211-F | ATA*CCATGG*CCACCATCATCATCATCATGAC GACGACGACAAGAAAAATCACCAGCAACAAA GTGCTCA (SEQ ID NO: 17) |
|  | XhoI-OXA-211-R | GAG*CTCGAG*TTAAATTATCCCCAGTGCTGTCAG ACTT (SEQ ID NO: 18) |
| OXA-229 | NdeI-HIS-EK-OXA-229-F | ATA*CATATG*CACCATCATCATCATCATGACGAC GACGACAAGCGAGAAACTGAGATTCCTTTATT ATT (SEQ ID NO: 19) |
|  | XhoI-OXA-229-R | GAG*CTCGAG*TTATCTTAAATAAAAAAATAGAC CCAATTTGT (SEQ ID NO: 20) |
| OXA-240 | NcoI-HIS-EK-OXA-240-F | CATATA*CCATGGG*CCACCATCATCATCATCATG ACGACGACGACAAGGGTTCAATTACAGAAAA TACGTC (SEQ ID NO: 21) |
|  | XhoI-OXA-240-R | CAGGAG*CTCGAG*TTAGCCACCAATGATGCCCA CA (SEQ ID NO: 22) |
| OXA-418 | NdeI-HIS-EK-OXA-418-F | ATA*CATATG*CACCATCATCATCATCATGACGAC GACGACAAGGGTTGTGTTTATGATTCAAAACT ACAA (SEQ ID NO: 23) |
|  | XhoI-OXA-418-R | GTG*CTCGAG*TTATCTTAAATAAAAAAATAGAC CCAATTTG (SEQ ID NO: 24) |

[a]F, sense (forward) primer; R, antisense (reverse) primer.
[b]Restriction sites appear in italic. The underlined bases indicate the hexahistidine tag site, and bold bases indicate the enterokinase recognition site.

Example 4

The Determination of IC$_{50}$ Values of the Inhibitor (PLPBA) for CHDLs

To investigate the inhibitory effects of the novel inhibitor (PLPBA) against eight CHDLs belonging to six clinically-important CHDL subgroups(member of OXA-23 subgroup: OXA-23; member of OXA-24/40 subgroup: OXA-24/40; member of OXA-48 subgroup: OXA-48; members of OXA-51 subgroup: OXA-51 and OXA-109; member of OXA-58 subgroup: OXA-97; member of OXA-143 subgroup: OXA-143) and five CHDLs belonging to four emerging CHDL subgroups (member of OXA-211 subgroup: OXA-211; members of OXA-229 subgroup: OXA-229 and OXA-418; member of OXA-210 subgroup: OXA-210; and member of OXA-240 subgroup: OXA-240), the IC$_{50}$ values for them were determined (Table 3). PLPBA was dissolved in 100% DMSO at 10 mM. More diluted stocks were prepared as necessary. Activities of CHDLs were determined by monitoring the change of absorbance at 482 nm. Up to 5% DMSO, no influence on the enzyme activities of CHDLs was observed. Each enzyme (OXA-23, 418 pM; OXA-24/40, 134 pM; OXA-48, 103 pM; OXA-51, 184 nM; OXA-97, 178 pM; OXA-109, 168 nM; OXA-143, 96 pM; OXA-210, 179 pM; OXA-211, 701 pM; OXA-229, 142 pM; OXA-240, 383 pM; OXA-418, 158 pM) was mixed with 100 μM nitrocefin after a 5 minute pre-incubation with PLPBA. The first 120 s of each reaction was used to measure initial rates. Data were evaluated using Microsoft Excel. Reaction progress at every concentration of PLPBA was measured in triplicates. The results of the inhibition of CHDLs by PLPBA are shown in Table 3. PLPBA showed $IC_{50}$ values in the 91.79±0.01 μM~864.59±0.02 μM ranges for twelve members of the clinically-important and emerging subgroups of CHDLs. In particular, PLPBA also showed $IC_{50}$ values in the 91.79±0.01 μM~594.73±0.01 μM ranges for seven members of the clinically-important subgroups of CHDLs.

TABLE 3

$IC_{50}$ values for novel inhibitor (PLPBA) against the clinically-important and emerging subgroups of CHDLs with nitrocefin as a substrate.

| Enzyme (CHDL[a]) | $IC_{50}$ (μM) | Enzyme (CHDL) | $IC_{50}$ (μM) |
| --- | --- | --- | --- |
| OXA-23 | 275.54 ± 0.02 | OXA-143 | 91.79 ± 0.01 |
| OXA-24/40 | 384.73 ± 0.02 | OXA-210 | 218.79 ± 0.02 |
| OXA-48 | 154.84 ± 0.02 | OXA-211 | 238.51 ± 0.01 |
| OXA-51 | 594.73 ± 0.01 | OXA-229 | 171.93 ± 0.01 |
| OXA-97 | 189.02 ± 0.01 | OXA-240 | 218.59 ± 0.03 |
| OXA-109 | 864.59 ± 0.02 | OXA-418 | 209.51 ± 0.02 |

[a]CHDL, carbapenem-hydrolyzing class D beta-lactamase

It was proven that the compound of Formula I shows broad-spectrum functionality to inhibit all six clinically important CHDLs subgroups and emerging CHDL subgroups.

What is claimed is:

1. A method of treating a bacterial infection, the method comprising:
   administering to a subject suffering from the bacterial infection a composition comprising an effective amount of a compound having Formula I or the pharmaceutically acceptable salt thereof:

<Formula I>

2. The method of claim 1, wherein the composition further comprises a beta-lactam antibiotic agent.

3. The method of claim 2, wherein the antibiotic agent is selected from the group consisting of penicillins, cephems, carbapenems, penems, and monobactams.

4. The method of claim 2, wherein the antibiotic agent is selected from the group consisting of penicillins, cephalosporins, cephamycins, monobactams, carbapenems, and a combination thereof.

5. The method of claim 1, further comprising administering a beta-lactam antibiotic agent to the subject.

6. The method of claim 5, wherein the antibiotic agent is selected from the group consisting of penicillins, cephalosporins, cephamycins, monobactams, carbapenems, and a combination thereof.

7. The method of claim 1, further comprising administering a beta-lactam antibiotic agent to the subject after administering the composition to the subject.

8. The method of claim 1, further comprising administering a beta-lactam antibiotic agent to the subject before administering the composition to the subject.

9. The method of claim 1, wherein the composition further comprises a pharmaceutically acceptable carrier.

10. The method of claim 1, wherein the infection is caused by pathogenic bacteria resistant to beta-lactam.

11. A method of inhibiting carbapenem-hydrolyzing class D beta-lactamases (CHDLs), the method comprising:
    preparing a composition having Formula I or a pharmaceutically acceptable salt thereof:

Formula I and
administering to a subject in need thereof the composition comprising an effective amount of the compound having Formula I or the pharmaceutically acceptable salt thereof,
wherein the carbapenem-hydrolyzing class D beta-lactamases comprises OXA-23, OXA-24/40, OXA-51, OXA-58, and OXA-143.

12. The method of claim 11, wherein the carbapenem-hydrolyzing class D beta-lactamases further comprises OXA-48, OXA-97, and OXA-109.

13. The method of claim 11, wherein the carbapenem-hydrolyzing class D beta-lactamases further comprises OXA-210, OXA-211, OXA-229, OXA-240, and OXA-418.

14. The method of claim 11, wherein the carbapenem-hydrolyzing class D beta-lactamases further comprises at least one selected from the group consisting of OXA-48, OXA-97, OXA-109, OXA-210, OXA-211, OXA-229, OXA-240, and OXA-418.

15. The method of claim 11, wherein the subject is infected with pathogenic bacteria resistant to beta-lactam.

16. The method of claim 15, wherein the beta-lactam is selected from the group consisting of penicillins, cephalosporins, cephamycins, monobactams, carbapenems, and a combination thereof.

17. The method of claim 11, wherein the composition further comprises a pharmaceutically acceptable carrier.

* * * * *